(12) United States Patent
Minev et al.

(10) Patent No.: US 10,448,514 B2
(45) Date of Patent: Oct. 15, 2019

(54) METHOD FOR THE ELECTRICAL PASSIVATION OF ELECTRODE ARRAYS AND/OR CONDUCTIVE PATHS IN GENERAL, AND A METHOD FOR PRODUCING STRETCHABLE ELECTRODE ARRAYS AND/OR STRETCHABLE CONDUCTIVE PATHS IN GENERAL

(71) Applicant: ECOLE POLYTECHNIQUE FEDERALE DE LAUSANNE (EPFL), Lausanne (CH)

(72) Inventors: Ivan Rusev Minev, Lausanne (CH); Stephanie P. Lacour, Daillens (CH)

(73) Assignee: Ecole Polytechnique Federale De Lausanne (EPFL), Lausanne (CH)

( * ) Notice: Subject to any disclaimer, the term of this patent is extended or adjusted under 35 U.S.C. 154(b) by 351 days.

(21) Appl. No.: 15/310,729

(22) PCT Filed: Jan. 8, 2015

(86) PCT No.: PCT/EP2015/050273
§ 371 (c)(1),
(2) Date: Nov. 11, 2016

(87) PCT Pub. No.: WO2015/172894
PCT Pub. Date: Nov. 19, 2015

(65) Prior Publication Data
US 2017/0086301 A1    Mar. 23, 2017

(30) Foreign Application Priority Data
May 13, 2014   (WO) .................. PCT/EP2014/059779

(51) Int. Cl.
*H01K 3/10*   (2006.01)
*H05K 3/00*   (2006.01)
(Continued)

(52) U.S. Cl.
CPC ......... *H05K 3/007* (2013.01); *A61B 5/04001* (2013.01); *A61N 1/0476* (2013.01);
(Continued)

(58) Field of Classification Search
CPC ............ H05K 3/007; H05K 3/12; H05K 3/28; H05K 3/005; H05K 3/4038;
(Continued)

(56) References Cited

U.S. PATENT DOCUMENTS

| 2004/0192834 A1 | 9/2004 | Nakayoshi et al. | |
| 2007/0009968 A1* | 1/2007 | Cunningham | B82Y 20/00 435/7.9 |

(Continued)

OTHER PUBLICATIONS

A. Cyganowski et al., "Stretchable electrodes for neuroprosthetic interfaces," Sensors, 2012 IEEE, Taipei, 2012, pp. 1-4 (Year: 2012).*

(Continued)

*Primary Examiner* — Thiem D Phan
(74) *Attorney, Agent, or Firm* — Seed IP Law Group LLP

(57) ABSTRACT

A method produces a conductive paste comprising 15-20% by weight of PDMS and 80-85% by weight of metallic micro-nano particles, wherein the conductive paste is obtained by repeated addition of singular doses of PDMS to a heptane diluted PDMS low viscosity liquid containing the metallic micro-nano particles, wherein the heptane fraction is allowed to evaporate after addition of each of the singular doses of PDMS. A method forms a conductive path on a support layer, wherein the conductive path is encapsulated by an encapsulation layer comprising at least one via through which at least one portion of the conductive path is exposed, the method comprising filling the at least one via with the conductive paste.

19 Claims, 9 Drawing Sheets

(51) Int. Cl.
*A61B 5/04* (2006.01)
*A61N 1/04* (2006.01)
*H05K 1/02* (2006.01)
*H01B 1/22* (2006.01)
*H05K 1/09* (2006.01)
*H05K 3/12* (2006.01)
*H05K 3/28* (2006.01)
*H05K 3/40* (2006.01)
*A61N 1/05* (2006.01)
*H01L 23/498* (2006.01)
*H01L 23/538* (2006.01)

(52) U.S. Cl.
CPC ............ *H01B 1/22* (2013.01); *H05K 1/0283* (2013.01); *H05K 1/092* (2013.01); *H05K 3/005* (2013.01); *H05K 3/12* (2013.01); *H05K 3/28* (2013.01); *H05K 3/4038* (2013.01); *A61B 2562/046* (2013.01); *A61B 2562/125* (2013.01); *A61N 1/0531* (2013.01); *A61N 1/0551* (2013.01); *H01L 23/4985* (2013.01); *H01L 23/5387* (2013.01); *H01L 2924/0002* (2013.01); *H05K 1/0272* (2013.01); *H05K 3/284* (2013.01); *H05K 2201/0133* (2013.01); *H05K 2201/0215* (2013.01); *H05K 2201/0257* (2013.01); *H05K 2201/0314* (2013.01); *H05K 2201/0329* (2013.01); *H05K 2203/1305* (2013.01); *H05K 2203/166* (2013.01); *Y10T 29/49165* (2015.01)

(58) Field of Classification Search
CPC ... H05K 2201/0329; H05K 2201/0257; H05K 2201/0215; H05K 2201/0133; H05K 2201/0314; H05K 1/092; H05K 1/0283; H05K 1/0272; H05K 2203/1305; H05K 2203/166; H05K 2201/09563; H05K 2203/308; H05K 1/115; H05K 2201/096; H05K 2201/09618; H05K 2203/0152; H05K 3/42; A61N 1/0476; A61N 1/0531; A61N 1/0551; A61N 5/04001; A61N 2562/046; H01B 1/22; A61B 5/04001; A61B 2562/046; H01L 23/5387; H01L 23/4985; H01L 2924/0002; Y10T 29/49146; Y10T 29/49155; Y10T 29/49165
USPC .................................. 29/852, 825, 829, 846
See application file for complete search history.

(56) References Cited

U.S. PATENT DOCUMENTS

| 2013/0041235 | A1 | 2/2013 | Rogers et al. |
| 2013/0345780 | A1 | 12/2013 | Tabada et al. |
| 2014/0124713 | A1 | 5/2014 | Majumdar et al. |

OTHER PUBLICATIONS

Meacham, K. W. et al., "A lithographically-patterned, elastic multi-electrode array for surface stimulation of the spinal cord," Biomed Microdevices 10:259-269, 2008.
Cyganowski, A. et al., "Stretchable Electrodes for Neuroprosthetic Interfaces," Sensors, 4 pgs., IEEE 2012.

\* cited by examiner

METHOD FOR THE ELECTRICAL PASSIVATION OF ELECTRODE ARRAYS AND/OR CONDUCTIVE PATHS IN GENERAL, AND A METHOD FOR PRODUCING STRETCHABLE ELECTRODE ARRAYS AND/OR STRETCHABLE CONDUCTIVE PATHS IN GENERAL

BACKGROUND

Technical Field

The present invention belongs to the field of electrode arrays and/or conductive paths or circuits in general. In particular, the present invention relates to a method for conveniently passivating and/or encapsulating electrode arrays or conductive paths in general, as well as to a method for producing and/or fabricating electrode arrays and/or conductive paths in general. Still in more detail, the present invention relates to a method for conveniently passivating stretchable electrode arrays, as well as to a method for producing and/or fabricating stretchable electrode arrays. According to the present invention there is further provided a method for producing a conductive material suitable for manufacturing electrode arrays or conductive paths in general, in particular for manufacturing stretchable electrode arrays, along with a conductive material produced according to the method and an electrode array or conductive path produced by using said conductive material. Still according to the present invention the conductive material is used for filling through vias in passivated conductive paths and/or electrode arrays.

Description of the Related Art

Electrode arrays and, in more general terms, conductive paths, require an insulation layer that covers the conductors so as to protect them from the environment in which they are used. The reason for that relates for example to the fact that, for some applications, the conductor arrays are immersed in a corrosive environment; a further reason, however, relates to the fact that the conductive paths have to be isolated from the environment and/or from each other, in order to prevent electrical interferences, crosstalk, short circuits or the like.

However, at least portions of the conductive paths and/or tracks have to be left uncovered or exposed for allowing the conductive paths to be electrically contacted; in general terms, said portions of the conductive paths define the contact pads and are usually located at the end of corresponding conductive paths; however, the openings may be formed anywhere along the conductive lines or paths, meaning that any portions of the conductive lines or paths may be used as corresponding contacting pads, according to the needs and/or circumstances.

There may even be one or several openings per line as well.

Accordingly, a need exists to passivate and/or insulate conductive paths, wherein portions of said conductive paths (the contact pads) are still exposed and therefore adapted to be electrically contacted.

Several passivation and/or encapsulation methods or processes have been proposed in the past in an attempt to face the need identified above.

For instance, according to the most common methods, an insulation layer is formed (for instance spin coated, laminated, deposited by chemical vapor deposition or the like) on an electrode array provided on a substrate, for instance a silicon wafer.

However, according to the known methods, a continuous film is formed; that means that, even if the thickness of the film (encapsulation layer) is arbitrary and may be selected according to the needs and/or circumstances, through vias have to be formed in the passivation layer or film for the purpose of exposing the active electrode sites (contact portions or pads) so as to allow same to be electrically contacted.

Still according to the prior art methods, said through vias are formed by means of complex lithography and/or etching steps.

However, even if said lithography and/or etching methods have revealed to be quite convenient for several reasons, (very small and/or precise vias may be open with a predefined shape and at predefined positions), said methods are still affected by several drawbacks and/or disadvantages.

One of said drawbacks relates in particular to the costs arising and to the complexity of the machinery and equipment needed for carrying out the above methods.

Moreover, a further drawback relates to the fact that organic solvents or even very aggressive physical or chemical etchants have to be used, which however can lead to damages of the conductors underneath or even, in the worst cases, to the partial or even complete removal of said conductors. Moreover, the chemicals etchants may also damage the carrier substrate or be absorbed by the substrate material (especially if it is a polymer).

In particular, avoiding the risk of damaging the conductors and/or substrate underneath represents an important challenge in the field of fabrication of elastic or stretchable electrode array, wherein the substrate is an elastomer and the thickness of the conductors or conductive paths amounts to a few, typically 1 to 100 nm.

Stretchable arrays (for instance stretchable gold microelectrode arrays, MEAs) are becoming more and more popular and find convenient applications in the field of wearable electrodes, and/or implantable neuroprosthetic interface applications, and/or as electrode arrays for cell culture and tissue slice culture, and/or even for sensing robotic skins or the like; in fact, the most important characteristic or feature of stretchtable microelectrode arrays (for instance MEAs), relates to the fact that same can withstand mechanical deformations such as flexing, stretching, torsion or the like, without electrical failure or loss of their electrical features (in particular electrical conductivity and impedance). Accordingly, microelectrode arrays (for instance MEAs) are particularly suitable to be used as a neural interface with the spinal cord, brain or peripheral nerves or soft biological tissue, for instance for the purpose of stimulating and/or recording neurological or cardiac activity (both in vitro and in vivo), as well as for monitoring hippocampal electrical activity after traumatic brain injury or bladder afferent activity, or even for stimulating electrical potential of excitable cells or the like.

It has in fact been verified that the impedance of microelectrode arrays stay low and stable during the deformation and even after repeated torsions, and therefore facilitate the recording of small amplitude biological signals and ensure efficient functional electrical stimulation. In particular, in both cases of in vitro and in vivo applications, SMEA did not show any degradation of the implant electrical interface, even after several months from implantation.

Microelectrode arrays are usually fabricated by thermally evaporating a metal (gold—Au) thin film on a soft PDMS (polydimethylsiloxane silicone substrate, 120 μm thick) using a polyimide shadow mask. The PDMS layer is cured at 80° C. for at least 12 hours. The resulting electrodes may be 50 μm wide, and mm to cm long, for instance. The connector pads may have an area of 1 mm² or smaller to allow for easier hand wiring later in the process. The metallization stack is composed of Ti/Au/Ti layers that are 5/30/3 nm thick, respectively, with the Ti layers used to improve adhesion.

It appears therefore clearly from the above that encapsulating the electrodes (whilst leaving the connector pads exposed) represents a difficult task due to the mandatory need of avoiding any risk of damaging the electrodes and/or connector pads.

BRIEF SUMMARY

It is therefore an object of the present invention that of overcoming or at least reducing the drawbacks affecting the prior art passivation and/or encapsulation methods.

In particular, an object of the present invention is that of proposing a method for passivating and/or encapsulating conductive paths or electrical circuits in general, adapted to be carried out at reduced and/or contained costs and without any need of using complex and/or expensive and/or bulky machinery or equipment and possibly without using liquid etchants; to the contrary, according to the present invention, the encapsulating process shall be a completely "dry" process.

Moreover, a further goal of the present invention is that of proposing an encapsulation and/or passivation method according to which chemical or physical agents like for instance solvents and/or etchants may be avoided.

Moreover, it belongs to the objects and/or goals of the present invention that of providing an encapsulation and/or passivation method or process allowing to establish a very strong and reliable bond (for instance a covalent bond) between the encapsulation layer and the conductive paths (or even between the conductive paths and the support layer on which same are formed) underneath.

Still a further object or goal of the present invention is that of proposing a method adapted in particular for encapsulating stretchable or soft microelectrode arrays (for instance MEAs), as well as a method particularly adapted for producing and/or fabricating the same.

It has moreover to be noted that a further challenge relating to the fabrication of stretchable electrodes, in particular those to be used as wearable electrodes, and/or for implantable neuroprosthetic interface applications, and/or even as electrode arrays for cell culture and tissue slice culture, and/or even for sensing robotic skins or the like, relates to the fact that, for these kinds of applications, the stretchable electrode arrays (in these cases also referred to as "bio-electrodes"), must be made, at least in part, of a biocompatible material with good charge injection properties. A conductive material showing these properties is Platinum (Pt) metal, at present used in the form of foils or wires; however, in this form, Pt cannot be integrated on ultra-compliant (stretchable) electrodes.

Accordingly, a further goal of the present invention is that of providing a Platinum-based conductive material in a form suitable to be used for manufacturing compliant or even ultra-compliant (stretchable or even ultra stretchable) electrodes or electrode arrays.

Still a further goal of the present invention is therefore that of providing a method for manufacturing electrode arrays (in particular stretchable electrode arrays), said method allowing convenient use of a platinum based material as summarized above.

The methods according to the present invention have revealed to be particularly suitable and/or convenient for passivating and fabricating stretchable microelectrode arrays, for instance MEAs.

Accordingly, this is the reason why, in the following, description will be given of examples according to which the methods according to the present invention are carried out for passivating, encapsulating and even producing and/or fabricating stretchable microelectrode arrays.

However, it has to be noted that the possible applications of the methods according to the present invention are not limited to the case of stretchable microelectrode arrays; to the contrary, the methods according to the present invention are adapted to be carried out for the passivation and/or encapsulation and even production or fabrication of any kind of electrical and/or electronic circuits or conductive paths.

The present invention is based on the consideration that the drawbacks affecting the passivation or encapsulation methods according to the prior art (at least those relating to the risk of damaging the conductors due to exposition to or contact with the etchants used for opening the vias into the passivation layer) may be efficiently and conveniently overcome by forming the passivation layer (comprising the through vias) separately from the electrodes or conductors array(s) and by bonding the previously prepared passivation layer to the conductors (or the layer or substrate underneath) once the vias have been adequately aligned with those portions of the conductors or conductive paths (in general the contact pads), which do not need to be encapsulated but have to stay uncovered or exposed. In this way, independently thereon which solution is used for forming the through vias, no risks arise to damage the conductors during formation of the vias. Moreover, expensive steps and machinery such as, for instance, those for photolithography, lamination, spraying, chemical vapour deposition, dry or whet etching or the like may be avoided.

In other words, whilst with the methods according to the prior art a continuous passivation layer is formed (for instance spin coated) directly on the conductors or conductive paths and the through vias are formed during a later step (with the risk arising of damaging the conductors), according to the present invention the passivation layer is deposited (formed) first on a support or layer other than that supporting the conductors.

A further consideration on which the present invention is based relates to the fact that further advantages arise by forming the passivation layer (with through vias) on a soft substrate other than the substrate which supports the conductors; in fact, with a soft substrate or layer supporting the passivation layer, the thickness of the passivation layer may be selected according to the needs and/or circumstances (the passivation layer may be as thin as needed), thus being the passivation layer particularly suitable for passivating very thin stretchable electrode arrays. Moreover, the vias may be easily formed according to any solution, for instance even using a very simple mechanical (punching) tool.

Still a further consideration on which the present invention is based relates to the fact that further advantages may be obtained when the passivation layer is formed by (comprises) two layers, namely a first and a second passivation layer (eventually with a release layer therebetween); in fact, the upper passivation layer may be used as a masking layer for filling the vias with conductive material once the entire passivation layer (comprising first and second passivation layers) has been placed on the conductors and the lower passivation layer has been bonded to same. In this way, by removing the upper passivation layer, conductive material eventually lying on same is removed too, thus obtaining an adequately passivated circuit or conductive path, wherein the through vias in the passivation layer are adequately filled with conductive material.

A further very important consideration on which the present invention is based relates to the fact that relevant results in terms of improved charge injection properties may be obtained by producing a platinum based conductive material in a form suitable for filling the through vias and by using same, accordingly, for filling the vias.

On the basis of the considerations as stated above, a first embodiment of the present invention relates to a method for encapsulating at least one conductive path formed on a support carrier, said method comprising:

forming an encapsulation layer on a substrate;
forming at least one through vias through said encapsulation layer;
aligning said at least one through vias with a predefined portion of said conductive path;
reciprocally bonding said encapsulation layer and said support carrier; and
removing said substrate.

Eventually, said substrate may comprise a transparent carrier to be removed once the encapsulation layer and the support carrier have been reciprocally bonded.

Conveniently, said transparent carrier may be removed.

Advantageously, said substrate may comprise a rubber (silicone) layer, and said encapsulation layer is formed on said rubber silicone layer, said rubber layer being peeled off from said encapsulation layer once said encapsulation layer has been bonded to said support carrier.

Preferably, the method further comprises functionalizing the upper surface of said rubber silicone layer with a non-stick release layer, and said encapsulation layer is deposited on said non-stick release layer.

Still preferably, said support carrier may comprise a soft and/or rubber layer formed on a rigid support, and said at least one conductive path is formed on said soft and/or rubber layer formed on said rigid support, wherein said encapsulation layer is bonded to said soft and/or rubber layer, said method further comprising removing said rigid support once said soft and/or rubber layer and said encapsulation layer have been reciprocally bonded.

Eventually, a non-stick release layer is formed between said rigid support and said soft and/or rubber layer.

According to a particular embodiment said at least one vias is formed by means of a mechanical punching tool and said at least one vias and said predefined portion of said conductive path are eventually aligned by looking through said transparent carrier (31).

To facilitate alignment of said at least one vias and said at least one portion of said at least one conductive path said transparent carrier and/or said support carrier may comprise alignment marks, and said at least one vias and said predefined portion of said conductive path are aligned by aligning said alignment marks.

A further embodiment of the present invention relates to a method forming at least a conductive path on a layer of a predefined material, said method comprising forming said layer of a predefined material on a rigid carrier and forming said at least one conductive path on said layer of a predefined material and encapsulating same according to the encapsulating method of the present invention.

Preferably, said predefined material comprises a soft and/or rubber (silicone) material.

Still preferably, said encapsulation layer comprises a first encapsulation layer and a second encapsulation layer, said method comprising peeling off said rubber silicone layer from said first encapsulation layer once said second encapsulation layer has been bonded to said support carrier.

Advantageously, said method further comprises filling said at least one vias with a conductive material and eventually peeling off said first encapsulation layer from said second encapsulation layer so as to remove conductive material outside said at least one vias.

Eventually, said conductive material may be a platinum based material produced according to a further method of the present invention.

Furthermore, said rigid carrier may be removed from said layer of soft and/or rubber material and said at least one conductive path may be evaporated on said layer of soft and/or rubber material.

According to the present invention there is still provided a method for producing a conductive material suitable in particular for filling the through vias, said method comprising mixing Pt micro-nano-particles with solvent thinned silicone rubber polymer so as to produce a conductive paste.

Further embodiments of the present invention are defined in the appended claims.

BRIEF DESCRIPTION OF THE SEVERAL VIEWS OF THE DRAWINGS

In the following, description will be given of the embodiments of the present invention depicted in the drawings. It has however to be noted that the present invention is not limited to the embodiments depicted in the drawings and described below; to the contrary, the present invention comprises all those embodiments which fall within the scope of the appended claims.

In the drawings.

DETAILED DESCRIPTION

Figure 1:
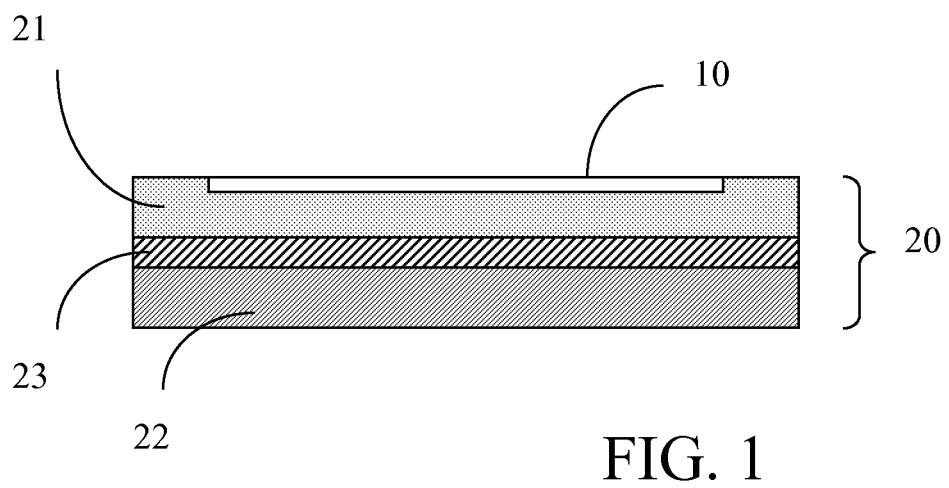
FIGS. 1, 2a to 2c, 3a to 3b and 4a to 4b depict method steps of a method according to a first embodiment of the present invention.

In FIGS. 1 to 4, the reference 10 identifies an electrode array, for instance a microelectrode array comprising at least one conductive path; in the following, for the sake of convenience and clarity, the electrode array 10 will be eventually simply referred to as a "conductive path" or "array of conductive paths". Said conductive paths 10 may be formed according to any of the methods known in the art such as, for instance, metal deposition of a continuous metal film ad etching, metal evaporation or the like. Since the particular method used for forming the conductive path 10 does not fall within the scope of the present invention, detailed description of same is omitted for the sake of conciseness.

The thickness of the layer carrying the 'array of conductive paths' is determined by the application requirements with thickness limitations of known methods for depositing such layers. By way of example for silicone rubber, the thickness of the layer can vary between 1 µm to 10 mm.

The conductive paths 10 are formed on a support carrier 20 comprising a rigid support or layer 22, for instance a silicon wafer 22. For those cases in which a soft or stretchable array of conductive paths has to be formed, the support carrier may comprise, as depicted in the drawings, a further soft and/or rubber layer 21, for instance a polydimethylsiloxane (PDMS) layer of a predefined thickness (about 100 μm). As further possible materials soft or flexible polymers such as polyurethane, polyimide, parylene may be cited. As a rigid inorganic material silicon or glass, by way of example, may be used. It has moreover to be noted that the thickness of the layer carrying the array(s) of conductive paths' is determined by the application requirements, wherein the thickness limitations depend on the methods carried out for depositing such layers. By way of example, for silicone rubber, the thickness of the layer can vary from 1 μm to 10 mm.

Still by way of example, the layer 21 may be spin coated on the rigid support 22 and cured, with excess PDMS material cut around the wafer.

Eventually, for purposes which will become more apparent with the following description, a release layer 23 may be formed between the rigid support 21 and the PDMS layer 21 to allow or at least facilitate late removal of the rigid support (silicon wafer) 22. By way of example, the release layer may comprise a water soluble layer such as spin coated Polyvinyl alcohol or polystyrene-sulphonic acid, or a self-assembled monolayer such as formed by 1H,1H,2H,2H-Perfluorooctyltriethoxysilane, or trimethylchlorosilane.

Figure 2A:
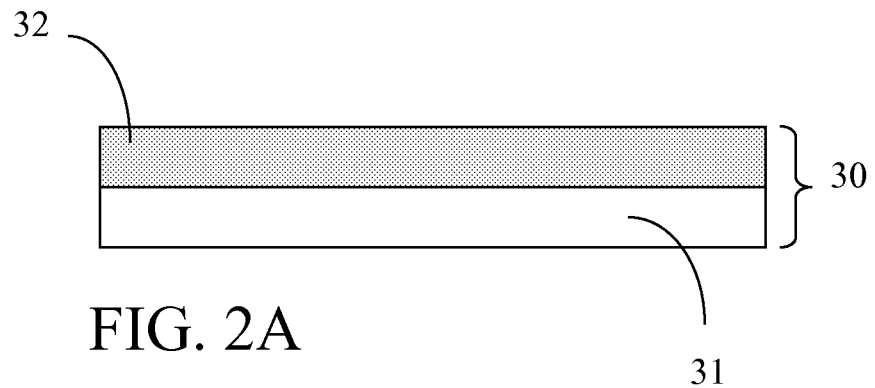
Figure 2B:
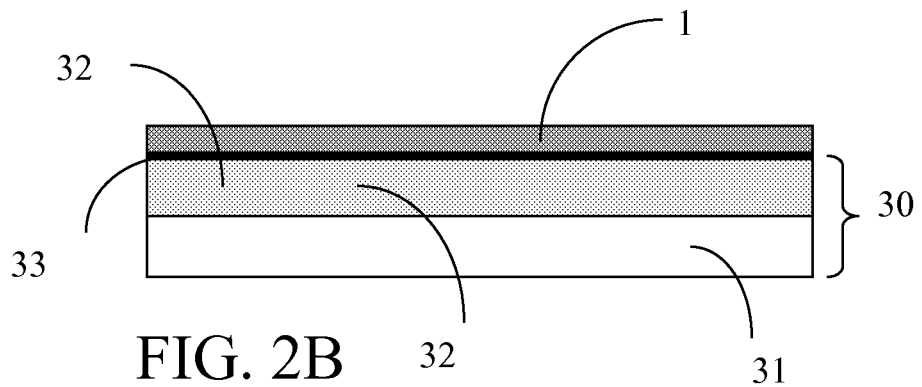
Figure 2C:
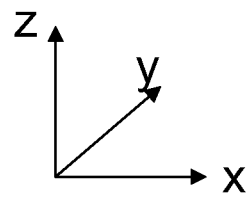
Figure 2C:
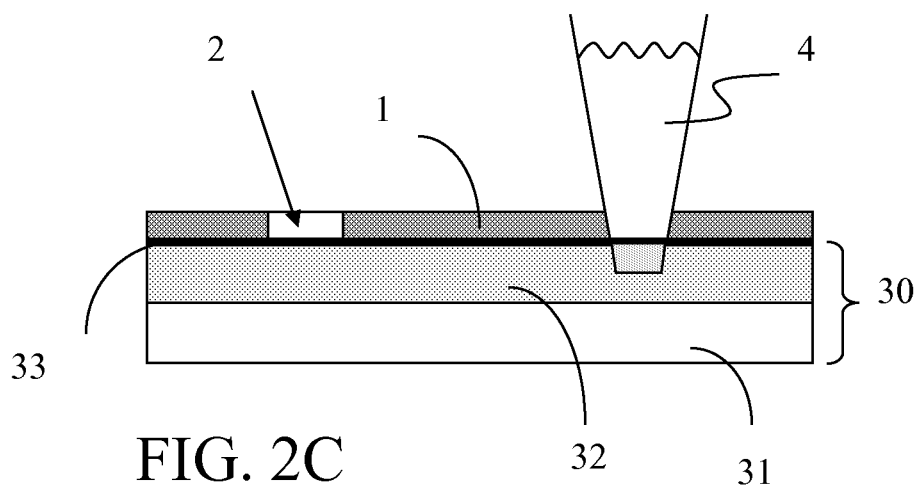

As depicted in FIGS. 2a to 2c, according to the method of the present invention depicted therein, a substrate 30 is provided, wherein said substrate 30 may comprise, as depicted, a transparent carrier 31, for instance a glass slice or wafer or substrate.

Whilst the purposes of the transparent carrier 31 will become more apparent with the following description, it may be noted, at this stage of the disclosure, that the substrate 30 comprises a further transparent layer 32, for instance a soft or rubber PDMS layer. For instance, said layer 32 may be spin coated on the carrier 31 and cured, with the excess PDMS material cut around the carrier 31. It will be appreciated in the light of the following description, that a soft or rubber layer 32 facilitates the formation of through vias in a passivation layer to be deposited on said layer 32. Within the scope of the present invention, the layer 32 may be made of silicone rubber, eventually transparent, such as, for instance, PDMS. By way of example the thickness of this layer may range from 4 to 10 mm.

As depicted in particular in FIG. 2b, a passivation or encapsulating layer 1 is formed on the layer 32; again, to this end, the layer 1 may be a silicone layer spin coated on the layer 32 and cured. In particular, in the case of silicone rubber, the convenient thicknesses range from 1 μm to 1 mm. However, other elastomers can be used for this layer such as, for instance, polyurethane or the like. Furthermore, an alternative method to form layer 1 is lamination.

Moreover, for allowing later removal of the layer 32, a non-stick release layer 33 may be formed between the layer 32 and the encapsulation layer 1; for instance, to this end, the upper surface of the layer 32 may be coated with a release layer such as that formed by a self-assembled monolayer of 1H,1H,2H,2H-Perfluorooctyltriethoxysilane or trimethylchlorosilane molecules.

Moreover, according to a further step of the method of the present invention as depicted in FIG. 2c, through vias 2 (at least one) are formed in the encapsulation layer 1. Within the meaning of the present invention, the expression "through vias" has to be understood as meaning through holes, meaning that at least a portion of the upper surface of the underlying layer 32 is exposed and no rests of said layer 1 are left inside the vias 2.

Moreover, within the scope of the present invention, the vias 2 may be formed according to any convenient solution, in particular, as depicted, using a simple punching tool (essentially a hollow needle) 4, wherein the inside of the needle or puncher 4 may be filled with a small amount of liquid to aid the removal of the encapsulation material 1.

The shape and dimension (diameter or the like) of the vias 2 will correspond to those of the punching tool 4, wherein vias of different shape and/or dimension may be formed by using corresponding different tools.

The layer 32, as anticipated above, not only facilitates the handling of the encapsulation layer 1 (see below), but also facilitates the formation of the vias, in particular in the special case in which same are formed by means of a punching tool 4 as depicted. In fact the layer 32 facilitates the puncher 4 to be inserted even beyond the encapsulation layer 1, meaning that the puncher 4 may be inserted to a depth which may be more than the thickness of the encapsulation layer 1.

It has further to be noted that, at this stage of the method according to the present invention, the encapsulation layer has not yet been put or disposed on the array 10 of conductive paths, but is still resting on layer 32, which simply acts as a support. Accordingly, the vias 2 may be formed as illustrated without any risk of damaging the conductive paths 10 to be passivated and/or encapsulated.

Figure 3A:
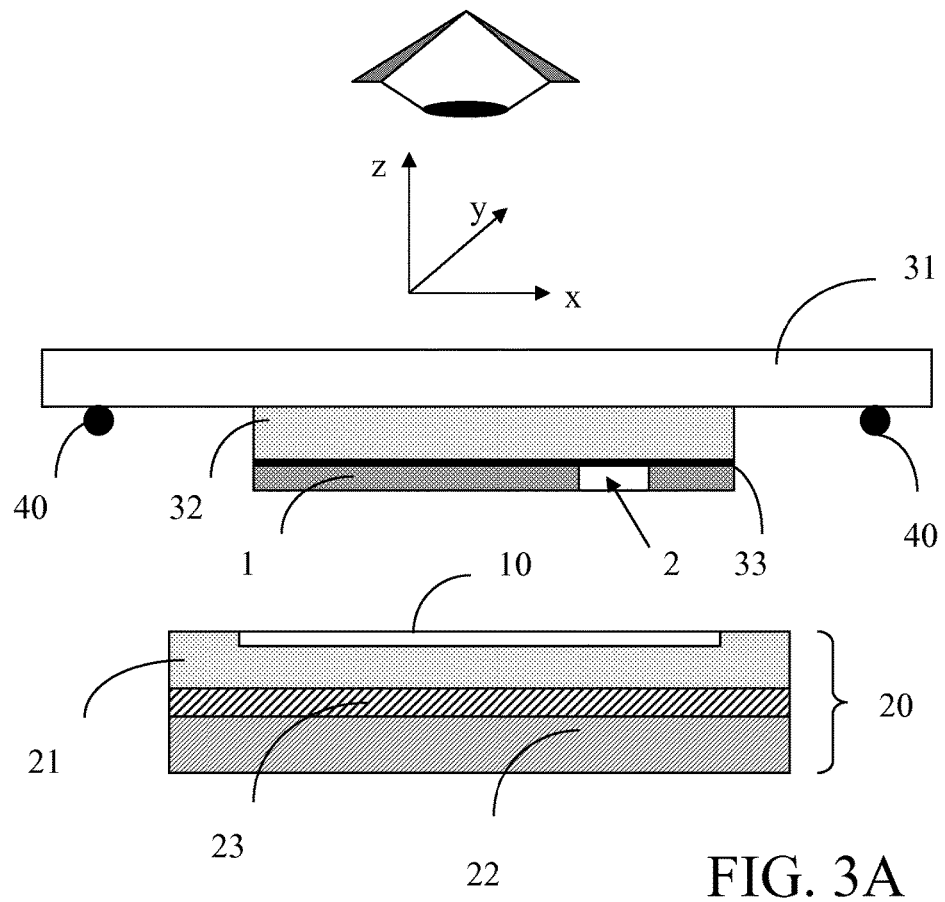
Figure 3B:
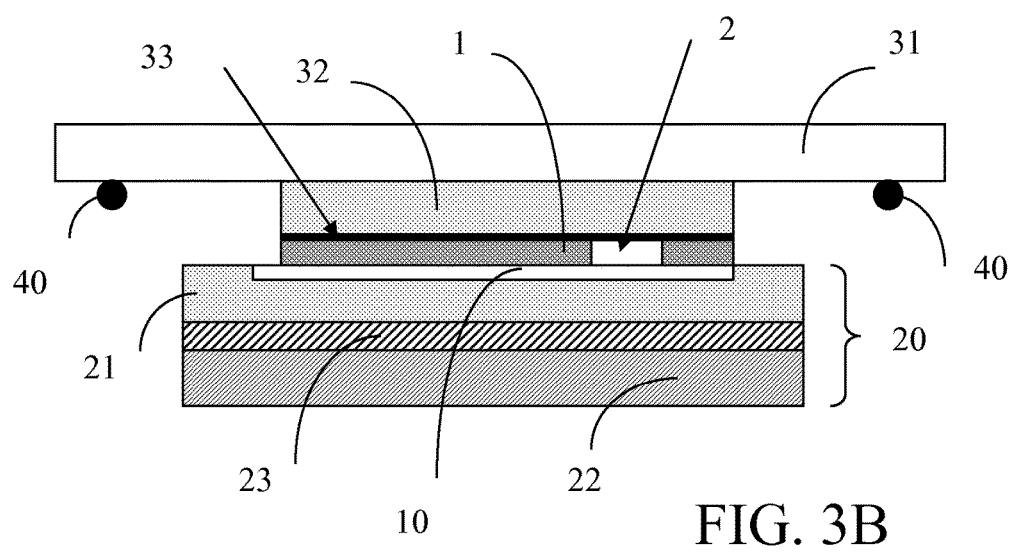

As depicted in particular in FIGS. 3a to 3b, the method according to the embodiment of the present invention depicted therein is prosecuted by inverting (flipping upside down) the stack comprising the layers 31 (if provided), 32, 33 (if provided) and 1 as depicted in FIG. 3a, and by aligning the vias 2 with predefined portions of the conductive paths 10, for instance those portions to be used as contact pads.

The alignment may be obtained even manually, for instance by means of a microscope, or eventually using an alignment tool (not depicted) either using alignment marks 40 (provided on at least one of the layers 31/32/33/1 and/or substrates 20/21, respectively. As a convenient alternative, the vias 2 and the corresponding portions of the conductive paths 10 may be aligned by simply looking through the transparent carrier 31.

Once the alignment has been completed as illustrated, during a further step (see FIG. 3b), the passivation layer 1 is brought into contact with the support carrier 20, meaning that portions of the passivation layer 1 will be brought into contact with the conductive paths 10, whilst portions of the passivation layer 1 will be brought into contact with the layer 21, with portions of the conductive paths (for instance those portions to be used as contact pads) in correspondence of the through vias 2 remaining uncovered and exposed.

Eventually, the passivation layer 1 may be strongly and reliably bonded to the layer 21 by exposing both layers to plasma surface activation, or by functionalisation of layers 1 and 21 with any pair of coupling agents before the aligning and bonding steps. By way of example, layer 1 can be functionalised with a self-assembled, covalently bonded monolayer of (3-Aminopropyl)triethoxysilane (APTES) and layer 21 with a self-assembled, covalently bonded monolayer of (3-Glycidyloxypropyl)trimethoxysilane (GPTES) which by way of contact between layers 1 and 21 will form a covalent bond assuring a permanent strong adhesion between layer 1 and 21.

Thus, at the stage depicted in FIG. 3b, the passivation layer 1 is bonded to the underlying layer 21, and portions of the conductive paths 10 are exposed through the open vias 2.

Figure 4A:
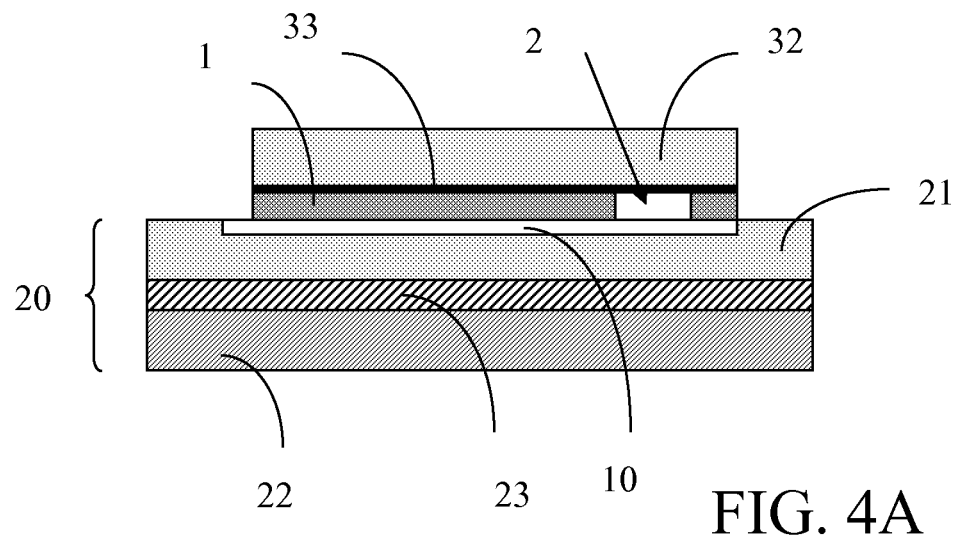
Figure 4B:
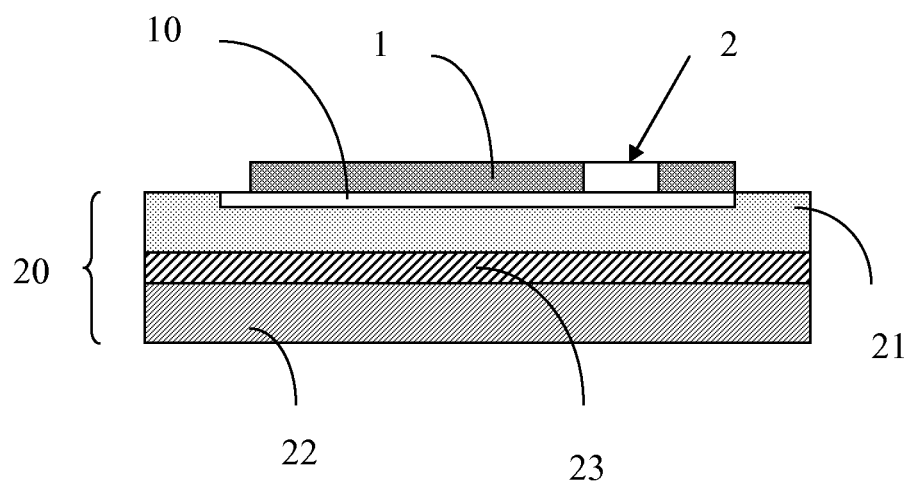

Accordingly, with further steps summarized in FIGS. 4a and 4b, the carrier and/or support layers may be removed; for instance the rigid and/or transparent carrier 31 and/or the soft or rubber layer 32 (if any) may be removed and peeled off, respectively, either singularly or together, wherein the removal and/or peeling off may be facilitated by non-stick release layers (in particular the release layer 33).

Finally, the rigid support (silicon wafer, for instance) 22 may be removed too, for instance using the release layer 23.

In this way, the resulting structure will comprise conductive paths 10 duly passivated by the passivation layer 1 (with vias 2), wherein said conductive paths are formed on a soft and/or stretchable (for instance PDMS) layer, meaning that a passivated stretchable array of conductive paths (for instance a stretchable microelectrode array) has been formed.

In the following, a further embodiment of a method according to the present invention will be described with references to FIGS. 5 to 9, wherein corresponding features are identified by corresponding reference numerals.

The method to be described below and depicted in FIGS. 5 to 9 differs from the method described above with reference to FIGS. 1 to 4 essentially due to the fact that a double passivation layer is used, namely a passivation layer 1 comprising first and second passivation sub layers, wherein by means of said first and second passivation layers a further step can be carried out in the process chain for producing conductive paths or microelectrode arrays, in particular stretchable microelectrode arrays, for instance MEAS (gold microelectrode arrays).

Figure 5A:
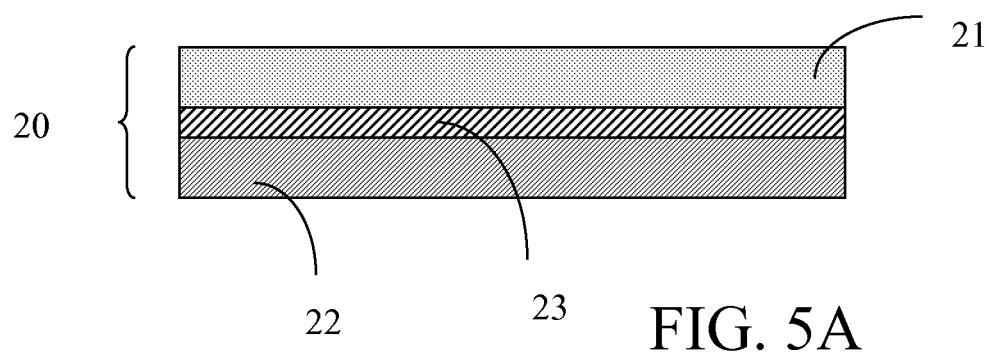
FIGS. 5a to 5b, 6a to 6c, 7a to 7b, 8a to 8b and 9a to 9b depict method steps of a method according to a further embodiment of the present invention.
Figure 5B:
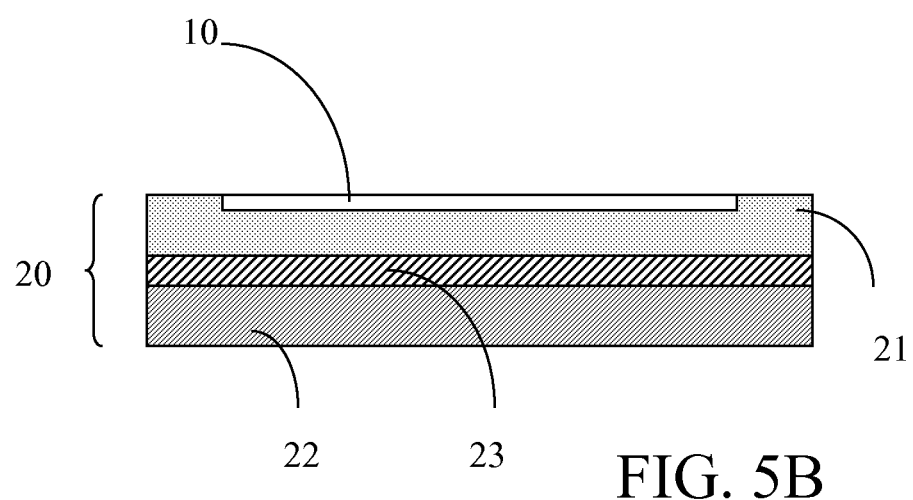

The starting situation is again that depicted in FIGS. 5a and 5b (corresponding to that of FIG. 1), with the only exception being that FIGS. 5a and 5b have to be understood a depicting a MEA, namely an array of conductive paths 10 formed on a stack comprising a rigid support 22 (for instance a silicon wafer), a soft or rubber layer 21 (for instance a PDMS layer) and eventually a release layer 23 therebetween.

By way of example, the microelectrode array 10 may be fabricated by thermally evaporating a metal (Au or Cr/Au) thin film on a soft PDMS (polydimethylsiloxane silicone substrate 21, 120 µm thick) using a shadow mask. The PDMS layer may be cured a 80° C. for a predefined time. The resulting electrodes may be 100 µm wide, and 13.5 mm long, for instance. The connector pads may have an area of 1 mm$^2$ to allow for easier hand wiring later in the process. The conductive paths 10 may be composed of Ti/Au/Ti layers that are 5/30/3 nm thick, respectively, with the Ti layers used to improve adhesion.

Figure 6A:
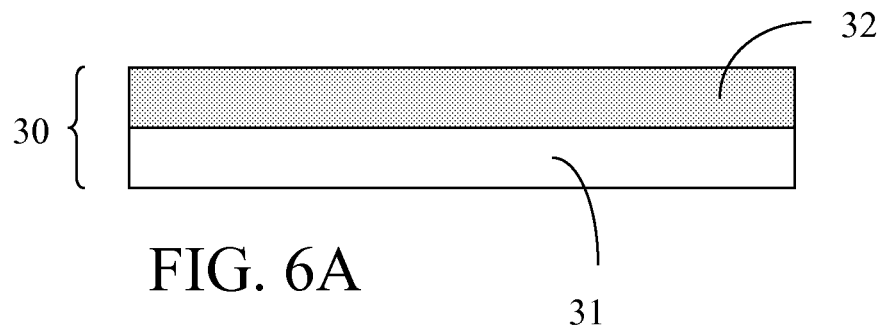
Figure 6B:
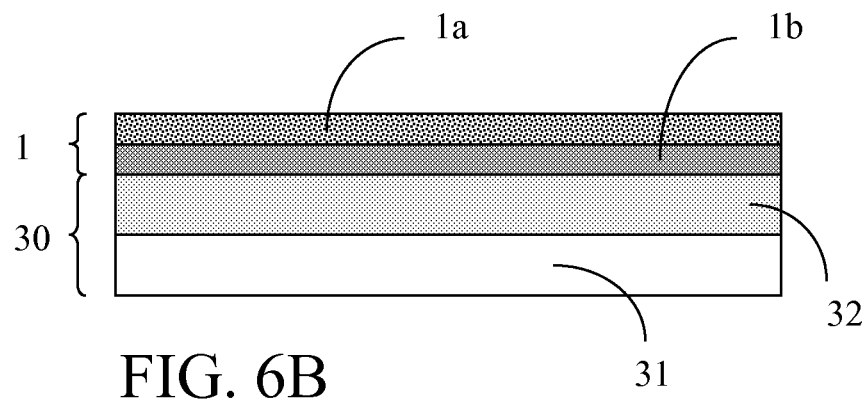
Figure 6C:
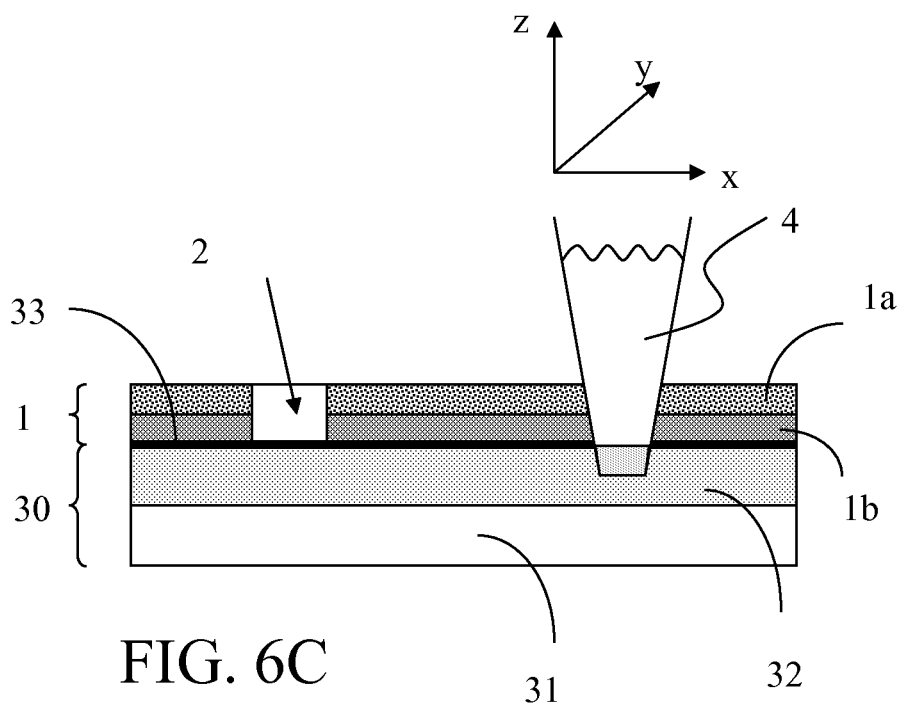

As depicted in FIGS. 6a to 6c, according to the embodiment of the method of the present invention depicted therein, a substrate 30 is provided again, wherein said substrate 30 may comprise, as depicted, a transparent carrier 31, for instance a glass slice or wafer.

The purposes of the transparent carrier 31 are the same as explained above with reference to the previous embodiment, wherein the substrate 30 may comprise again a further layer 32, for instance a soft or rubber PDMS layer. For instance, said layer 32 may be spin coated on the carrier 31 and cured, with the excess PDMS material cut around the carrier 31, wherein the soft or rubber layer 32 facilitates again the formation of through vias in a passivation layer to be deposited on said layer 32. However, within the scope of the present invention, the layer 32 may be made of transparent silicone rubber such as PDMS. By way of example the thickness of this layer may range from 4 to 10 mm.

As depicted in particular in FIG. 6b, a passivation or encapsulating layer 1 is formed on the layer 32, wherein however, in this case, the passivation layer 1 comprises a first passivation layer 1b and a second passivation layer 1a;

again, each of said first and second passivation layers 1b, 1a may be a silicon layer spin coated on the layer 32 and cured. In particular, in the case of silicone rubber the convenient thicknesses for layers 1a and 1b may range from 1 µm to 1 mm. Alternatively, other elastomers can be used such as, for example, polyurethane or the like. An alternative method to form layer 1 is lamination.

Moreover, for allowing later removal of one or both of the layers 32 and 1b, non-stick release layers (one non-stick release layer 33 being depicted) may be formed between the layers 32 and 1b, as well as between the encapsulation layers 1a and 1b, respectively; for instance, to this end, the upper surface of each of the layers 32 and 1b may be coated with a release layer such as that formed by a self-assembled monolayer of 1H,1H,2H,2H-Perfluorooctyltriethoxysilane or trimethylchlorosilane molecules.

Moreover, according to a further step of the method according to the embodiment of the present invention as depicted in FIG. 6c, through vias 2 (at least one) are formed in the encapsulation layer 1, meaning through the encapsulation layers 1a and 1b. Again, within the meaning of the present invention, the expression "through vias" has to be understood as meaning through holes, meaning that at least a portion of the upper surface of the underlying layer 32 is exposed and no remains of said layer 1a and 1b are left inside the vias 2.

As in the case of the previous embodiment, within the scope of the present invention, the vias 2 may be formed according to any convenient solution, in particular, as depicted, using a simple punching tool (essentially a hollow needle) 4, wherein the inside of the needle or puncher 4 may be filled with a small amount of liquid to aid the removal of the encapsulation material 1 (1a and 1b).

The shape and dimension of the vias 2 will correspond again to those of the punching tool 4, wherein vias of different shape and/or dimension may be formed by using corresponding different tools.

Again, the layer 32 not only facilitates the handling of the encapsulation layer 1 (see below), but also facilitates the formation of the vias 2, in particular in the special case in which same are formed by means of a punching tool 4 as depicted. In fact the layer 32 facilitates the puncher 4 to be inserted even beyond the encapsulation layers 1a and 1b, meaning that the puncher 4 may be inserted to a depth which may be more than the thickness of the encapsulation layers 1a and 1b.

It has further to be noted again that, at this stage of the method according to this embodiment of the present invention, the encapsulation layers 1a and 1b have not yet been put or disposed on the conductive paths 10, but are still resting on the layer 32, which simply acts as a support.

Figure 7A:
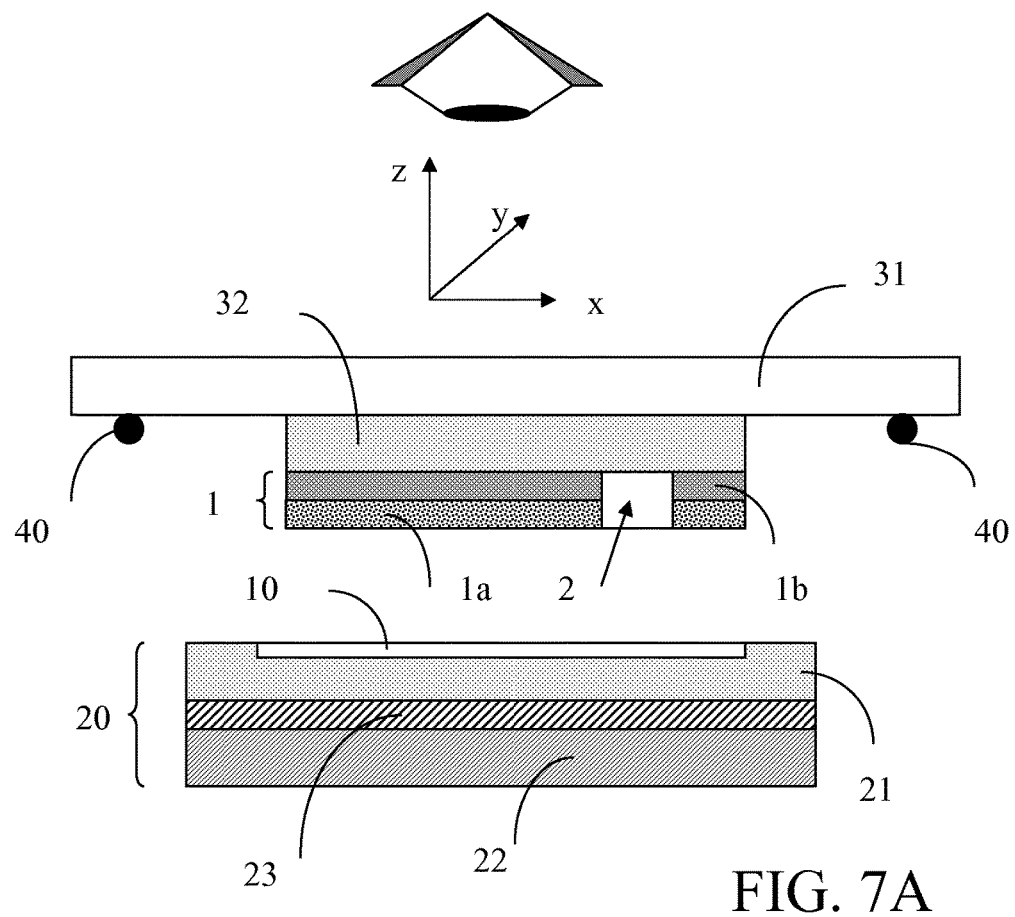
Figure 7B:
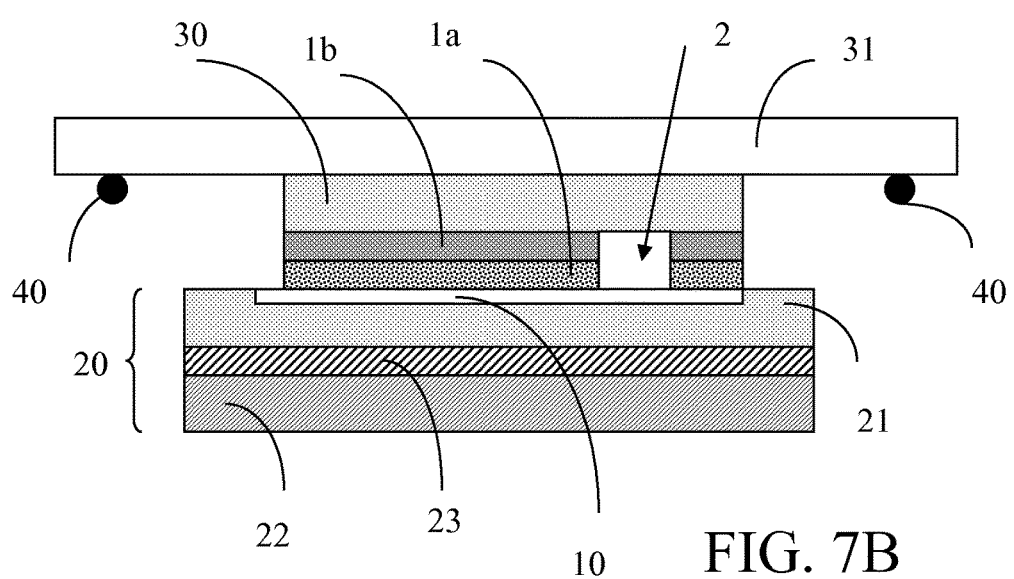
Figure 8A:
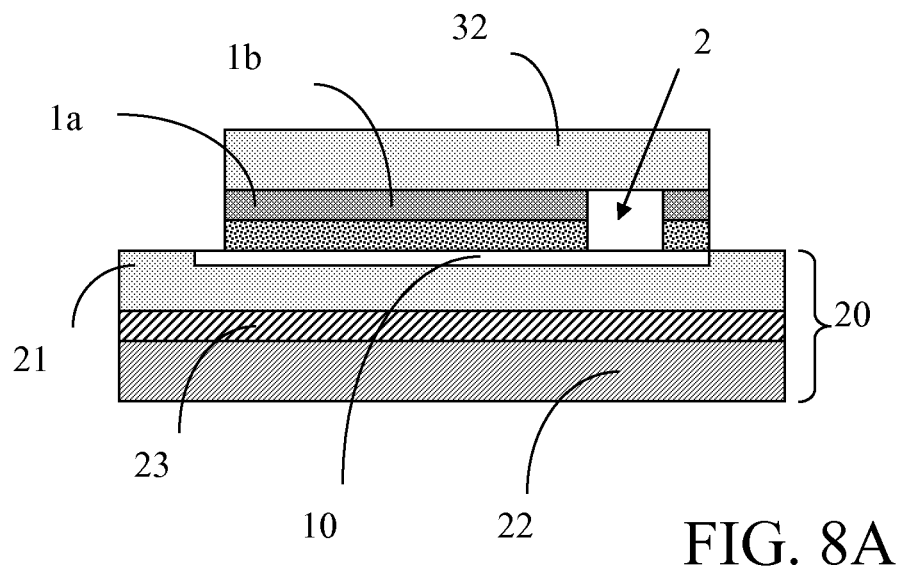
Figure 8B:
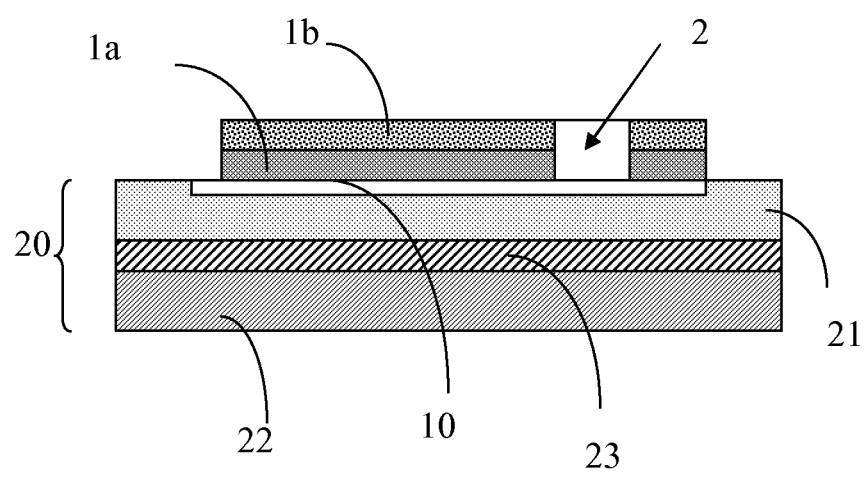

Also the method according to this embodiment of the present invention is prosecuted by carrying out the method steps depicted in FIGS. 7a, 7b and 8a, these steps comprising in particular:

inverting (flipping upside down) the stack comprising the layers 31 if any), 32, 33 (if any) and 1 and aligning the vias 2 with predefined portions of the conductive paths 10, for instance those portions to be used as contact pads (FIG. 7a);

bringing into contact the passivation layer 1 with the support carrier 20, meaning bringing the passivation layer 1a into contact with the conductive paths 10 and/or layer 21 and bonding the passivation layer 1a and the layer 21 (FIG. 7b);

removing the carrier and/or support layers (the rigid and/or transparent carrier 31 and/or the soft or rubber layer 32 (if any).

Since the above steps may be carried out according to the same solutions and/or alternatives already described above with reference to FIGS. 3a, 3b and 4a, a further detailed description of same is omitted for the sake of conciseness.

The resulting structure will therefore comprise again (see FIG. 8b) conductive paths 10 duly passivated by the passivation layers 1a and 1b (with vias 2).

Figure 9A:
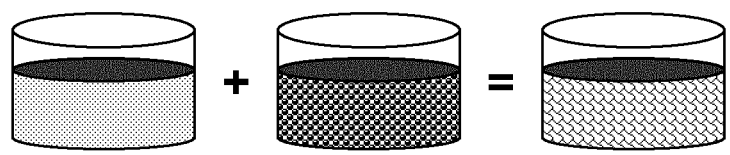
Figure 9A:
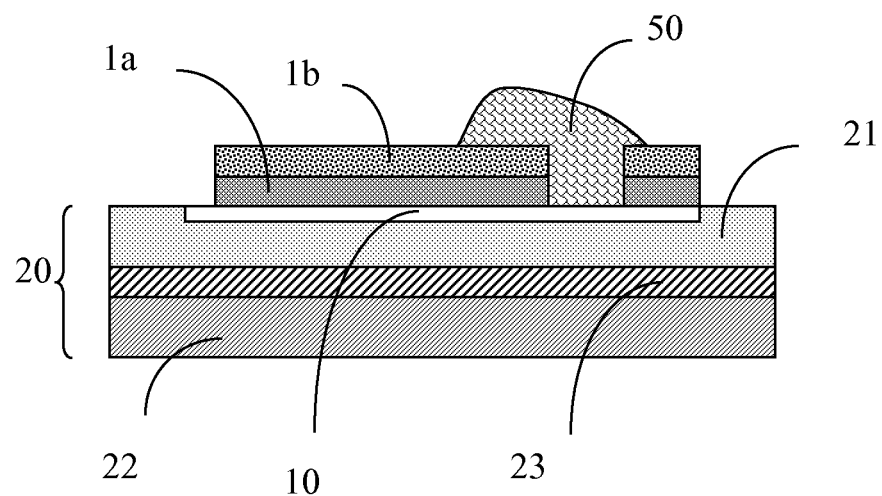
Figure 9B:
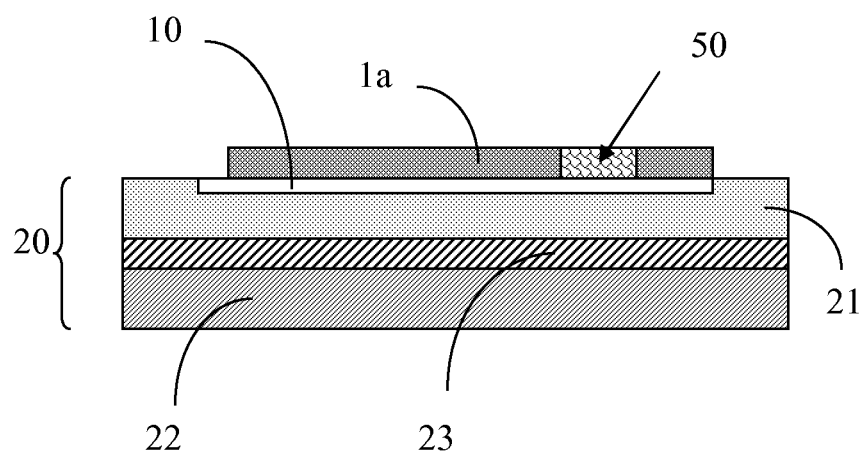

The method is than prosecuted by carrying out the further steps of same as depicted in FIGS. 9a and 9b.

In particular, as depicted in FIG. 9a, the vias are filled with conductive material 50.

Finally, during a further step as depicted in FIG. 9b, the first encapsulation layer 1b is peeled off from the second encapsulation layer 1a, thus removing also excess of conductive material 50 eventually lying on the layer 1b outside the vias.

The resulting structure is therefore a duly passivated array of conductive paths 10, eventually formed on a stretchable layer, wherein the contacting vias 2 are already filled with conductive material 50.

A method having been described for manufacturing electrode arrays, said method comprising in particular filling the vias with a conductive material, description will be given in the following of a further method according to the present invention by means of which a convenient conductive material is produced, said conductive material allowing easy filling of the vias and showing improved mechanical and electromechanical characteristics (such as improved stretchability, biocompatibility, improved charge injection properties or the like), The conductive material or composite prepared according to the following description is a blend of platinum nano-micro particles and PDMS silicone.

According to the method, a PDMS pre-polymer (for instance composed of organosilicon monomers or oligomers which are capable of further reactions to form high molecular weight polymers) is mixed with its cross-linker. In its pre-polymer form PDMS has the consistency of honey, flows easily (5000 cP) and is stable. The cross-linker initiates the polymerization reaction which transforms the oligomers into high molecular weight chains of polydimethylsiloxane. When the curing reaction is completed (usually several hours later), the result is the elastomer.

As an example, both pre-polymer and cross-linker may be of the kind as supplied by the manufacturer (Dow Corning). In particular, a possible ratio of the products used may be 10:1 prepolymer:crosslinker. However, within the frame of the present invention, other similar two component elastomer kits are possible, for example based on polyurethanes, even if their high viscosity (1000 s cP) prior to curing makes mixing with the metallic micro particles more difficult.

Moreover, once mixed with its cross-linker, the PDMS is diluted in heptane in a 1:2 w:w ratio, until a low viscosity liquid is obtained. It has however to be noted that different ratios are also possible, as long as 1:>2 (for example 1:3); adding more heptane lowers the viscosity, more time being needed for its evaporation, accordingly.

The procedure is then prosecuted by adding 100 mg of platinum microparticles to 5 mg of the PDMS based low viscosity liquid (or, in other words, to 15 µL of the heptane diluted PDMS). In particular, platinum powder with particles size between 0.5 µm and 1.2 µm may be conveniently used, The mixture is then thoroughly stirred (for instance by hand for approximately. a minute long using a cocktail stick) and put aside for evaporation of the heptane fraction (for instance until Ideally no heptane is left).

As an example, for the purpose of evaporating the heptane fraction, the mixture may be left at room temperature (for approximately 10 minutes) to avoid the PDMS starting to cross-link. However, using an oven at a predefined temperature higher than the room temperature also falls within the scope of the present invention.

The addition of 5 mg amounts (also referred to as singular doses) of PDMS is repeated (on average four times, wherein after each addition evaporation of the heptane fraction is allowed (as described above).

No further PDMS is added once the mixture becomes a paste, wherein paste formation occurs once the PDMS content corresponds to 15-20% by weight and the heptane has substantially fully evaporated.

The conductive paste obtained according to the above described method revealed to be particularly useful for filling conductive vias, for instance as described with reference to FIGS. 9A and 9B. In particular, the paste showed improved filling properties, along with excellent stretchability and charge injection. It has however to be noted that the paste allows the vias to be filled in a very simple way, for instance by spreading and pressing the paste, even manually, on the encapsulation layer 1b wherein, eventually and according to the needs and/or circumstances, the paste may be temporarily thinned with a drop of pure heptane, wherein the amount of heptane to be used depends on the amount of paste to be diluted or used. As an example, for the whole 100 mg of Pt, 10-20 µl of pure heptane may be used.

It has therefore been demonstrated with the above description that methods according to the present invention allow to obtain the wished results, thus overcoming the drawbacks affecting the prior art methods.

Whilst the present invention has been clarified by means of the above description of its embodiments depicted in the drawings, the present invention is not limited to the embodiments depicted in the drawings and/or described above.

For instance, the use of micro-nano particles of one or more of platinum, iridium, iridium oxide and/or other similar metals and/or metal oxides falls within the scope of the present invention.

The scope of the present invention is rather defined by the appended claims.

The invention claimed is:

1. A method for encapsulating a conductive path formed on a support carrier, said method comprising:
    forming an encapsulation layer on a substrate, wherein said substrate comprises a transparent carrier;
    forming at least one through via through said encapsulation layer;
    aligning said at least one through via with a predefined portion of said conductive path;
    reciprocally bonding said encapsulation layer and said support carrier;
    comprising removing said transparent carrier once said encapsulation layer and said support carrier have been reciprocally bonded;
    forming a silicone rubber layer on said transparent carrier;
    forming said encapsulation layer on said silicone rubber layer; and
    peeling off said silicone rubber layer from said encapsulation layer once said encapsulation layer has been bonded to said support carrier.

2. The method as claimed in claim 1, said method further comprising functionalizing an exposed surface of said silicone rubber layer with a non-stick release layer, wherein said encapsulation layer is deposited on said non-stick release layer.

3. The method as claimed in claim 1, wherein said support carrier comprises a soft or rubber layer formed on a rigid support, wherein said conductive path is formed on said soft or rubber layer formed on the rigid support, wherein said encapsulation layer is bonded to said soft or rubber layer, said method further comprising removing said rigid support once said soft or rubber layer and said encapsulation layer have been reciprocally bonded.

4. The method as claimed in claim 3, wherein a non-stick release layer is formed between said rigid support and said soft or rubber layer.

5. The method as claimed in claim 1, wherein said at least one via is formed by a mechanical punching tool.

6. The method as claimed in claim 1, wherein said substrate comprises a transparent carrier and said at least one via and said predefined portion of said conductive path are aligned by looking through said transparent carrier, said method further comprising removing said transparent carrier once said encapsulation layer and said support carrier have been reciprocally bonded.

7. The method as claimed in claim 1, wherein said substrate comprises a transparent carrier and both said transparent carrier and said support carrier comprise alignment marks, and wherein said at least one via and said predefined portion of said conductive path are aligned by aligning said alignment marks, said method further comprising removing said transparent carrier once said encapsulation layer and said support carrier have been reciprocally bonded.

8. A method, comprising:
forming a soft or rubber material layer on a rigid support carrier
forming a conductive path on said soft or rubber material layer;
forming an encapsulation layer on a substrate, wherein said substrate comprises a transparent carrier;
forming at least one through via through said encapsulation layer;
aligning said at least one through via with a predefined portion of said conductive path;
reciprocally bonding said encapsulation layer and said support carrier;
removing said transparent carrier after reciprocally bonding said encapsulation layer and said support carrier;
forming a silicone rubber layer on said transparent carrier;
forming said encapsulation layer on said silicone rubber layer; and
peeling off said silicone rubber layer from said encapsulation layer after reciprocally bonding said encapsulation layer and said support carrier.

9. The method as claimed in claim 8, wherein said encapsulation layer comprises a first encapsulation layer and a second encapsulation layer, said method comprising peeling off said soft or rubber material layer from said first encapsulation layer once said second encapsulation layer has been bonded to said support carrier.

10. The method as claimed in claim 9, further comprising peeling off said first encapsulation layer from said second encapsulation layer so as to remove conductive material outside said at least one via.

11. The method as claimed in claim 8, said method further comprising filling said at least one via with a conductive material.

12. The method as claimed in claim 11, wherein said conductive material is a conductive paste comprising 15-20% by weight of polydimethylsiloxane (PDMS) and 80-85% by weight of metallic micro-nano particles.

13. The method according to claim 12, wherein said conductive paste is obtained by repeated addition of singular doses of PDMS to a heptane diluted PDMS low viscosity liquid containing said metallic micro-nano particles, wherein the heptane is allowed to evaporate after addition of each of said singular doses of PDMS.

14. The method as claimed in claim 13, wherein the heptane diluted PDMS low viscosity liquid containing said metallic micro-nano particles is obtained by adding 100 mg of metallic micro-nano particles to 15 μL of said heptane diluted PDMS low viscosity liquid.

15. The method according to claim 12, wherein said conductive paste is spread on said first encapsulation layer and pressed into said at least one via.

16. The method according to claim 12, wherein said metallic micro-nano particles comprise micro-nano particles of one or more of platinum, iridium, iridium oxide.

17. The method according to claim 11, wherein the metallic micro-nano particles are sized between 0.5 μm and 1.2 μm.

18. The method as claimed in claim 8, further comprising removing said rigid carrier from said soft or rubber material layer.

19. The method as claimed in claim 8, wherein said conductive path is evaporated on said layer of soft or rubber material.

* * * * *